United States Patent [19]

Fujita et al.

[11] Patent Number: 4,912,123
[45] Date of Patent: Mar. 27, 1990

[54] ANTIFUNGAL AND MILDEWPROOFING IMIDAZOLE COMPOUNDS

[75] Inventors: Takayuki Fujita, Matsushige; Yoshiya Iwasaki, Kitajima; Hiroko Yabe; Tadashi Akita, both of Tokushima, all of Japan

[73] Assignee: Shikoku Chemicals Corporation, Kagawa, Japan

[21] Appl. No.: 263,266

[22] Filed: Oct. 27, 1988

[30] Foreign Application Priority Data

Oct. 27, 1987 [JP] Japan .................. 62-272685

[51] Int. Cl.⁴ .................. A01N 43/50; C07D 409/06; C07D 409/14
[52] U.S. Cl. ..................... 514/397; 548/336
[58] Field of Search ............. 548/336; 514/397

[56] References Cited

U.S. PATENT DOCUMENTS 4,720,551  1/1988  Fujita et al. .................. 548/336

OTHER PUBLICATIONS

Chemical Abstracts, 107:134307s(1987)[EP 218,398, Fujita et al., 4/15/87].

Primary Examiner—Richard A. Schwartz
Attorney, Agent, or Firm—Sherman and Shalloway

[57] ABSTRACT

Disclosed is a novel imidazole compound represented by the following formula:

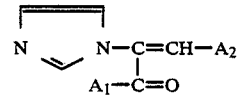

wherein $A_1$ stands for a thien-3-yl or 4-chlorophenyl group and $A_2$ stands for a 2,4-dichlorophenyl, 2-chlorothien-3-yl or 2-chloro-5-bromothien-3-yl group, with the proviso that at least one of $A_1$ and $A_2$ stands for a thien-3-yl or halogen-substituted thien-3-yl group. This compound is effective as a therapeutic antifungal agent or mildewproofing agent.

7 Claims, No Drawings

ANTIFUNGAL AND MILDEWPROOFING IMIDAZOLE COMPOUNDS

BACKGROUND OF THE INVENTION (1) Field of the Invention

The present invention relates to a novel imidazole compound and a process for the preparation thereof. Furthermore, the present invention relates to an antifungal agent and a mildewproofing agent, which comprise this novel imidazole compound. More particularly, the present invention relates to an imidazole compound which is valuable as a therapeutic antifungal agent.

(2) Description of the Related Art

It is known that certain imidazole compounds have a fungicidal action. For example, Japanese Patent Publication No. 16479/68 discloses 1-hydroxy-2-undecyl-3-methylimidazolium-p-toluene-sulfonate, 1-benzyl-2-undecyl-3-methylimidazolium methylsulfate and 1-dodecyl-2-ethyl-3-benzylimidazolium chloride as fungicidal agents. Furthermore, the specification of U.S. Pat. No. 4,577,032 discloses 1-benzyldibromomethyl-2-methylimidazole. The compound of the present invention has a much broader antimicrobial spectrum than those of these known compounds.

SUMMARY OF THE INVENTION

The imidazole compound of the present invention is represented by the following general formula (1):

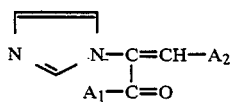

(1)

wherein $A_1$ stands for a thien-3-yl or 4-chlorophenyl group and $A_2$ stands for a 2,4-dichlorophenyl, 2-chlorothien-3-yl or 2-chloro-5-bromothien-3-yl group, with the proviso that at least one of $A_1$ and $A_2$ stands for a thien-3-yl or halogen-substituted thien-3-yl group.

This compounds represented by the general formula (1) can be prepared by reacting an imidazolylethanone compound represented by the following general formula (2):

(2)

wherein $A_1$ is as defined above, with an aldehyde compound represented by the following general formula (3):

(3)

wherein $A_2$ is as defined above.

Among compounds represented by the general formula (1), the following imidazole compounds are especially preferred:

1-(thien-3-yl)-2-(1H-imidazolyl)-3-(2,4-dichlorophenyl)-2-propen-1-one of the following formula:

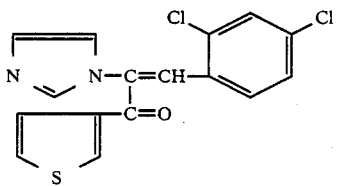

(I)

1-(thien-3-yl)-2-(1H-imidazolyl)-3-(2-chlorothien-3-yl)-2-propen-1-one of the following formula:

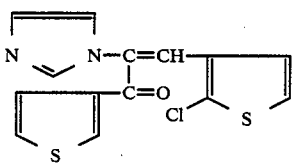

(II)

1-(4-chlorophenyl)-2-(1H-imidazolyl)-3-(2-chlorothien-3-yl)-2-propen-1-one of the following formula:

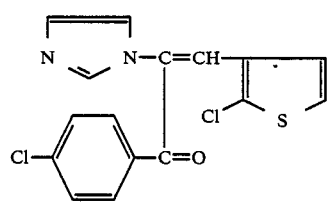

(III)

1-(4-chlorophenyl)-2-(1H-imidazolyl)-3-(2-chloro-5-bromothien-3-yl)-2-propen-1-one of the following formula:

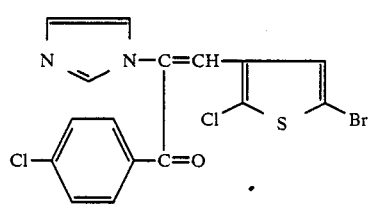

(IV)

DETAILED DESCRIPTION OF THE INVENTION

The imidazole compound of the present invention can be prepared by refluxing 1 mole of the imidazolylethanone compound of the formula (2) and 1 to 2 moles of the aldehyde compound of the formula (3) in a solvent such as benzene in the presence of piperidine for 1 to 10 hours. After completion of the reaction, the reaction liquid is concentrated and the reaction product is eluted with a solvent such as chloroform or chloroform/methyl alcohol by the silica gel chromatography, and the eluate is crystallized by using a solvent such as isopropyl ether or n-hexane and recrystallized from a solvent such as ethyl acetate or ethyl acetate/n-hexane. Thus, the intended imidazole compound can be obtained.

The compounds of the present invention are characterized in that they are in the form of white or yellow crystals, neutral or weakly acidic, hardly soluble in water and soluble in ethyl acetate, n-hexane and dimethyl sulfoxide.

These compounds have a relatively broad antimicrobial spectrum and are valuable as fungicidal agents, and they are particularly effective when used as antifungal agents or mildewproofing agents.

The present invention will now be described in detail with reference to the following examples that by no means limit the scope of the invention.

EXAMPLE 1

Preparation of 1-(thien-3-yl)-2-(1H-imidazolyl)-3-(2,4-dichlorophenyl)-2-propen-1-one.

In the presence of piperidine, 1.37 g of 1-(thien-3-yl)-2-(1H-imidazolyl)ethane and 1.87 g of 2,4-dichlorobenzaldehyde was refluxed in benzene for 7 hours. After completion of the reaction, the reaction liquid was concentrated and the reaction product was eluted with chloroform by the silica gel chromatography, and the eluate was crystallized and precipitated by using isopropyl ether and the crystals were recrystallized from ethyl acetate/isopropyl ether to obtain 0.64 g of a white crystal having a melting point of 102° to 103° C.

From the results of the analysis, it was confirmed that the product was 1-(thien-3-yl)-2-(1H-imidazolyl)-3-(2,4-dichlorophenyl)-2-propen-1-one represented by the following structural formula, and the yield was 26%.

Structural Formula:

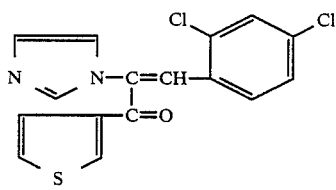

Elementary Analysis Values (%): Found values: C=54.75, H=2.66, N=7.54 Calculated values: C=55.04, H=2.89, N=8.02.

Nuclear Magnetic Resonance Analysis (chloroform-d, ppm): 7.77 (1H, s, 2-position of imidazole), 7.73 (1H, m, 2-position of thiophene), 7.28-7.58 (4H, m, 4,5-positions of thiophene, C=CH—, 3-position of 2,4-dichlorobenzene), 7.18 (2H, s, 4,5-positions of imidazole), 6.91 (1H, m, 5-position of 2,4-dichlorobenzene), 6.61 (1H, d, 6-position of 2,4-dichlorobenzene).

EXAMPLE 2

Preparation of 1-(thien-3-yl)-2-(1H-imidazolyl)-3-(2-chlorothien-3-yl)-2-propen-1-one.

In the presence of piperidine, 1.25 g of 1-(thien-3-yl)-2-(1H-imidazolyl)ethanone and 0.95 g of 2-chloro-3-thiophene aldehyde were refluxed in benzene for 2.5 hours. After completion of the reaction, the reaction liquid was concentrated and the reaction product was eluted with chloroform/methanol by the silica gel chromatography. The eluate was crystallized by using n-hexane and the crystals were recrystallized from ethyl acetate/n-hexane to obtain 0.56 g of a light brown crystal having a melting point of 116° to 118° C.

From the results of the analysis, it was confirmed that the product was 1-(thien-3-yl)-2-(1H-imidazolyl)-3-(2-chlorothien-3-yl)-2-propen-1-one represented by the following structural formula, and the yield was 27%.

Structural Formula:

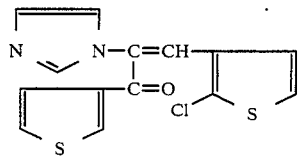

Elementary Analysis Values (%): Found values: C=52.12, H=2.68, N=8.29 Calculated values: C=52.41, H=2.83, N=8.73.

Nuclear Magnetic Resonance Analysis (chloroform-d/dimethylsulfoxide-d6, ppm): 7.72-8.05 (3H, m, 2-position of thiophene, C=CH—, 2-position of imidazole), 7.48 (2H, m, 4,5-positions of thiophene), 7.19 (2H, s, 4,5-positions of imidazole), 7.10 (1H, d, 5-position of 2-chlorothiophene), 5.79 (1H, d, 4-position of 2-chlorothiophene).

EXAMPLE 3

Preparation of 1-(4-chlorophenyl)-2-(1H-imidazolyl)-3-(2-chlorothien-3-yl)-2-propen-1-one.

In the presence of piperidine, 3.00 g of 1-(4-chlorophenyl)-2-(1H-imidazolyl)ethanone and 2.00 g of 2-chloro-3-thiophene aldehyde were refluxed in benzene for 8 hours.

The reaction product was treated in the same manner as described in Example 2 to obtain 1.60 g of a light yellow crystal having a melting point of 137° to 139° C.

From the results of the analysis, it was confirmed that the product was 1-(4-chlorophenyl)-2-(1H-imidazolyl)-3-(2-chlorothien-3-yl)-2-propen-1-one having the following structural formula, and the yield was 34%.

Structural Formula:

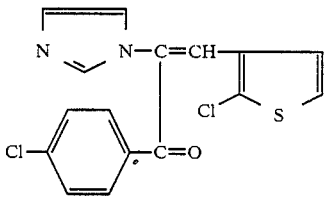

Elementary Analysis Values (%): Found values: C=55.01; H=2.79, N=7.88 Calculated values: C=55.04, H=2.89, N=8.02.

Nuclear Magnetic Resonance Analysis (chloroform-d, ppm): 7.55 (1H, s, 2-position of imidazole), 7.51 (1H, s, C=CH—), 7.35-7.83 (4H, each d, 3,5-positions of 4-chlorobenzene, 2,6-positions of 4-chlorobenzene), 7.26 and 6.95 (1H, s, 4- or 5-position of thiophene), 5.83 (1H, d, 4-position of thiophene).

EXAMPLE 4

Preparation of 1-(4-chlorophenyl)-2-(1H-imidazolyl)-3-(2-chloro-5-bromothien-3-yl)-2-propen-1-one.

In the presence of piperidine, 1.96 g of 1-(4-chlorophenyl)-2-(1H-imidazolyl)ethanone and 2.00 g of 2-chloro-5-bromo-3-thiophene aldehyde were refluxed in benzene for 8.5 hours.

The reaction product was treated in the same manner as described in Example 2 to obtain 1.60 g of a light yellow crystal having a melting point of 155° to 157° C.

From the results of the analysis, it was confirmed that the product was 1-(4-chlorophenyl)-2-(1H-imidazolyl)-3-(2-chloro-5-bromothien-3-yl)-2-propen-1-one represented by the following structural formula, and the yield was 42%.

Structural Formula:

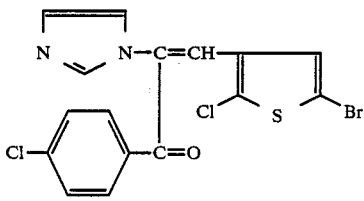

Elementary Analysis Values (%): Found values: C=45.80, H=2.25, N=6.36 Calculated values: C=44.88, H=2.12, N=6.54.

Nuclear Magnetic Resonance Analysis (chloroform-d, ppm): 7.36–7.76 (6H, m, 2-position of imidazole, aromatic), 7.29 and 6.25 (2H, each, s, 4,5-positions of imidazole), 5.73 (1H, d, 4-position of thiophene).

EXAMPLE 5

With respect to the compounds obtained in the foregoing examples, the minimum growth inhibiting concentrations to pathogenic bacterial were measured. The obtained results are shown in Table 1. The unit of each value in Table 1 is μg/ml. The used pathogenic bacteria were *Candida albicans, Trichophyton rubrum, Trichophyton mentagrophytes, Trichophyton tonsurans* and *Microsporum gypsum*. Culturing was conducted in Sabouraud's agar culture medium at 25° C. The growth of the bacterium was checked at intervals of 24 hours after inoculation. The minimum concentration at which no colony was formed was measured as the minimum inhibitory concentration after the passage of 7 days.

TABLE 1

| Compound of Present Invention | Candida albicans | Trichophyton rubrum | Trichophyton mentagrophytes | Trichophyton tonsurans | Microsporum gypseum |
|---|---|---|---|---|---|
| Example 1 | 6.25 | <0.39 | <0.39 | <0.39 | 0.39 |
| Example 2 | 25 | 1.56 | 3.13 | 3.13 | 12.5 |
| Example 3 | 12.5 | 0.78 | 3.13 | 1.56 | 6.25 |
| Example 4 | 12.5 | <0.39 | <0.39 | 0.78 | 12.5 |

We claim:

1. A imidazole compound represented by the following formula:

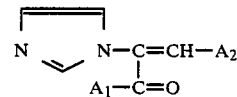

wherein $A_1$ stands for a thien-3-yl or 4-chlorophenyl group and $A_2$ stands for a 2,4-dichlorophenyl, 2-chlorothien-3-yl or 2-chloro-5-bromothien-3-yl group, with the proviso that at least one of $A_1$ and $A_2$ stands for a thien-3-yl or halogen-substituted thien-3-yl group.

2. 1-(Thien-3-yl)-2-(1H-imidazolyl)-3-(2,4-dichlorophenyl)-2-propen-1-one.

3. 1-(Thien-3-yl)-2-(1H-imidazolyl)-3-(2-chlorothien-3-yl)-2-propen-1-one.

4. 1-(4-Chlorophenyl)-2-(1H-imidazolyl)-3-(2-chlorothien-3-yl)-2-propen-1-one.

5. 1-(4-Chlorophenyl)-2-(1H-imidazolyl)-3-(2-chloro-5-bromothien-3-yl)-2-propen-1-one.

6. An antifungal composition comprising an effective amount of an imidazole compound as set forth in claim 1 and a carrier therefor.

7. A mildewproofing composition comprising an effective amount of an imidazole compound as set forth in claim 1 and a carrier therefor.

* * * * *